US010526594B2

(12) United States Patent
Greiner-Stoeffele et al.

(10) Patent No.: US 10,526,594 B2
(45) Date of Patent: *Jan. 7, 2020

(54) RECOMBINANTLY PRODUCED NEUTRAL PROTEASE ORIGINATING FROM PAENIBACILLUS POLYMYXA

(71) Applicant: Roche Diagnostics Operations, Inc., Indianapolis, IN (US)

(72) Inventors: Thomas Greiner-Stoeffele, Soemmerda (DE); Stefan Schoenert, Leipzig (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,658

(22) Filed: Oct. 26, 2016

(65) Prior Publication Data

US 2017/0037390 A1    Feb. 9, 2017

Related U.S. Application Data

(63) Continuation of application No. 14/592,969, filed on Jan. 9, 2015, now abandoned, which is a continuation of application No. PCT/EP2013/064271, filed on Jul. 5, 2013.

(30) Foreign Application Priority Data

Jul. 9, 2012   (EP) .................................... 12175563

(51) Int. Cl.
| | |
|---|---|
| *C12N 9/54* | (2006.01) |
| *C12N 9/52* | (2006.01) |
| *C07K 14/195* | (2006.01) |
| *C12N 5/071* | (2010.01) |

(52) U.S. Cl.
CPC ............. *C12N 9/52* (2013.01); *C07K 14/195* (2013.01); *C12N 5/0602* (2013.01); *C12Y 304/24* (2013.01); *C12Y 304/24028* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 3,930,954 | A | 1/1976 | Irie |
| 4,304,966 | A | 12/1981 | Green et al. |
| 5,762,502 | A | 6/1998 | Bahn et al. |
| 5,830,741 | A | 11/1998 | Dwulet et al. |
| 2006/0269527 | A1 | 11/2006 | Nilsson et al. |

FOREIGN PATENT DOCUMENTS

| | | |
|---|---|---|
| EP | 2161333 A1 | 3/2010 |
| WO | 1998/024889 A1 | 6/1998 |
| WO | 2009/140343 A1 | 11/2009 |

OTHER PUBLICATIONS

International Search Report dated Sep. 2, 2013 in Application No. PCT/EP2013/064271, 7 pages.
Honjo, Masaru et al., "Cloning and expression of the gene for neutral protease of Bacillus amyloliquefaciens in Bacillus subtilis," Journal of Biotechnology, 1984, pp. 265-277, vol. 1.
Ikram-Ul-Haq and Mukhtar, Hamid, "Studies on the Optimization of Protease Production by Bacillus Subtilis IH-16," Proceedings of the Pakistan Congress of Zoology, 2004, pp. 67-75, vol. 24.
Mansfeld, Johanna et al., "The propeptide is not required to produce catalytically active neutral protease from Bacillus stearothermophilus," Protein Expression and Purification, 2005, pp. 219-228, vol. 39.
Matta, Hittu and Punj, Vasu, "Isolation and partial characterization of a thermostable extracellular protease of Bacillus polymyxa B-17," International Journal of Food Microbiology, 1998, pp. 139-145, vol. 42.
Murao, Sawao et al., "β-Amylases from Bacillus polymyxa No. 72," Agriculture, Biology and Chemistry, 1979, pp. 719-726, vol. 43, No. 4.
Ruf, Armin et al., "Structure of Gentlyase, the neutral metalloprotease of Paenibacillus polymyxa," Acta Crystallographica Section D, 2013, pp. 24-31, vol. D69.
Stenn, Kurt S. et al., "Dispase, a Neutral Protease From Bacillus Polymyxa, Is a Powerful Fibronectinase and Type IV Collagenase," Journal of Investigative Dermatology, 1989, pp. 287-290, vol. 93.
Takekawa, Shiro et al., "Proteases Involved in Generation of β- and α-Amylases from a Large Amylase Precursor in Bacillus polymyxa," Journal of Bacteriology, Nov. 1991, pp. 6820-6825, vol. 173, No. 21.
Twentyman, Peter R. and Yuhas, John M., "Use of a Bacterial neutral protease for Disaggregation of Mouse Tumours and Multicellular Tumour Spheroids," Cancer Letters, 1980, pp. 225-228, vol. 9.
Wang, Lin-Fa and Devenish, Rodney J., "Expression of Bacillus subtilis Neutral Protease gene (nprE) in *Saccharomyces cerevisiae*," Journal of General Microbiology, 1993, pp. 343-347, vol. 139.
UNIPROT:E3E6L0, "Subname: Full=Bacillolysin," 2013, retrieved from EBI accession No. UNIPROT:E3E6L0, 1 page.

*Primary Examiner* — David Steadman
(74) *Attorney, Agent, or Firm* — Stinson LLP

(57) ABSTRACT

The present disclosure provides the sequence of a Paenibacillus polymyxa preproenzyme which is the precursor of a neutral protease, expression thereof in a transformed host organism, and methods for production of the neutral protease, by recombinant means. Further, use of the recombinantly produced neutral protease is disclosed in the field of cell biology, particularly for the purpose of tissue dissociation. The disclosure also includes blends with other proteases. Further disclosed are nucleotide sequences encoding the neutral protease.

7 Claims, 1 Drawing Sheet
Specification includes a Sequence Listing.

```
Seq-1   1   MKKVWFSLLGGAMLLGSVASGASAESSVSGPAQLTPTFHTEQWKAPSSVSGDDIVWSYLN
            MKKVW SLLGGAMLLGSVASGASAESSVSGP QLTPTFH EQWKAPSSVSGDDIVWSYLN
Seq-2   1   MKKVWVSLLGGAMLLGSVASGASAESSVSGPTQLTPTFHAEQWKAPSSVSGDDIVWSYLN

Seq-1  61   RQKKSLLGVDSSSVREQFRIVDRTSDKSGVSHYRLKQYVNGIPVYGAEQTIHVGKSGEVT
            RQKKSLLG D SSVREQFRIVDRTSDKSGVSHYRLKQYVNGIPVYGAEQTIHVGKSGEVT
Seq-2  61   RQKKSLLGADDSSVREQFRIVDRTSDKSGVSHYRLKQYVNGIPVYGAEQTIHVGKSGEVT

Seq-1 121   SYLGAVINEDQQEEATQGTTPKISASEAVYTAYKEAAARIEALPTSDDTISKDAEEPSSV
            SYLGAV+ EDQQ EATQGTTPKISASEAVYTAYKEAAARIEALPTSDDTISKD EE SSV
Seq-2 121   SYLGAVVTEDQQAEATQGTTPKISASEAVYTAYKEAAARIEALPTSDDTISKDVEEQSSV

Seq-1 181   SKDTYAEAANNDKTLSVDKDELSLDKASVLKDSKIEAVEAEKSSIAKIANLQPEVDPKAE
            SKDTYAEAANN+KTLS DKDELSLDKAS LKDSKIEAVEAEKSSIAKIANLQPEVDPKA+
Seq-2 181   SKDTYAEAANNEKTLSTDKDELSLDKASALKDSKIEAVEAEKSSIAKIANLQPEVDPKAD

Seq-1 241   LYYYPKGDDLLLVYVTEVNVLEPAPLRTRYIIDANDGSIVFQYDIINEATGTGKGVLGDS
            LY+YPKGDDL LVYVTEVNVLEPAPLRTRYIIDANDGSIVFQYDIINEATGTGKGVLGD+
Seq-2 241   LYFYPKGDDLQLVYVTEVNVLEPAPLRTRYIIDANDGSIVFQYDIINEATGTGKGVLGDT

Seq-1 301   KSFTTTASGSSYQLKDTTRGNGIVTYTASNRQSIPGTLLTDADNVWNDPAGVDAHAYAAK
            KSFTTTASGSSYQLKDTTRGNG+VTYTASNRQSIPGT+LTDADNVWNDPAGVDAH YAAK
Seq-2 301   KSFTTTASGSSYQLKDTTRGNGVVTYTASNRQSIPGTILTDADNVWNDPAGVDAHTYAAK

Seq-1 361   TYDYYKSKFGRNSIDGRGLQLRSTVHYGSRYNNAFWNGSQMTYGDGDGDGSTFIAFSGDP
            TYDYYK+KFGRNSIDGRGLQLRSTVHYGSRYNNAFWNGSQMTY GDGDGSTFIAFSGDP
Seq-2 361   TYDYYKAKFGRNSIDGRGLQLRSTVHYGSRYNNAFWNGSQMTY--GDGDGSTFIAFSGDP

Seq-1 421   DVVGHELTHGVTEYTSNLEYYGESGALNEAFSDVIGNDIQRKNWLVGDDIYTPNICGDAL
            DVVGHELTHGVTEYTSNLEYYGESGALNEAFSDVIGNDIQRKNWLVGDDIYTPNI GDAL
Seq-2 419   DVVGHELTHGVTEYTSNLEYYGESGALNEAFSDVIGNDIQRKNWLVGDDIYTPNIAGDAL

Seq-1 481   RSMSNPTLYDQPHHYSNLYKGSSDNGGVHTNSGIINKAYYLLAQGGTFHGVTVNGIGRDA
            RSMSNPTLYDQP HYSNLY GSSDNGGVHTNSGIINKAYYLLAQGGTFHGVTVNGIGRDA
Seq-2 479   RSMSNPTLYDQPDHYSNLYTGSSDNGGVHTNSGIINKAYYLLAQGGTFHGVTVNGIGRDA

Seq-1 541   AVQIYYSAFTNYLTSSSDFSNARAAVIQAAKDLYGANSAEATAAAKSFDAVG--
            AVQIYYSAFTNYLTSSSDFSNARAAVIQAAKD YGANSAEATAAAKSFDAVG
Seq-2 539   AVQIYYSAFTNYLTSSSDFSNARAAVIQAAKDQYGANSAEATAAAKSFDAVGVN
```

RECOMBINANTLY PRODUCED NEUTRAL PROTEASE ORIGINATING FROM PAENIBACILLUS POLYMYXA

RELATED APPLICATIONS

This application is a continuation of U. S. application Ser. No. 14/592,969 filed Jan. 9, 2015, which is a continuation of International Application No. PCT/EP2013/064271 filed Jul. 5, 2013, which claims priority to European Application No. 12175563.1 filed Jul. 9, 2012, the disclosures of which are hereby incorporated by reference in their entirety.

FIELD OF THE INVENTION

The present disclosure provides the sequence of a Paenibacillus polymyxa preproenzyme which is the precursor of a neutral protease, expression thereof in a transformed host organism, and methods for production of the neutral protease, by recombinant means. Further, use of the recombinantly produced neutral protease is disclosed in the field of cell biology, particularly for the purpose of tissue dissociation. The disclosure also includes blends with other proteases. Further disclosed are nucleotide sequences encoding the neutral protease, as well as fragments thereof.

The present invention is directed to the means for providing a recombinantly expressed and enzymatically active neutral protease from *Paenibacillus polymyxa*, also known as Dispase®. Particularly, an amino acid sequence is provided which is suited for large-scale production by way of recombinant expression thereof, specifically and with particular advantage in transformed *Bacillus* species serving as a recombinant host strain. In a specific embodiment, recombinantly expressed Paenibacillus polymyxa neutral protease is secreted into liquid culture medium and purified therefrom.

BACKGROUND

From filtrates or supernatants of *Paenibacillus polymyxa* cultures (*P. polymyxa;* formerly also known as *Bacillus polymyxa* or *B. polymyxa,* all these taxonomic names are used synonymously herein), a neutral protease was isolated and characterized. In the more recent literature the neutral protease is often referred to as "Dispase®", which is a registered trademark of Godo Shusei Co., Ltd., Tokyo, Japan. Owing to fibronectinase and type IV collagenase proteolytic activity, technical utility of Dispase® is known particularly in the field of animal cell or tissue culture. Thus, dissociation of a tissue (including cell clumps or cell aggregates) into cell layers or even suspensions of single cells is frequently performed with the activity of this enzyme, either with Dispase® alone or with Dispase® as a component of blends, i.e. combined other proteolytic enzymes, specifically Collagenases, e.g. as disclosed in U.S. Pat. No. 5,830,741.

U.S. Pat. No. 3,930,954 discloses a neutral protease from *B. polymyxa* strain having the accession number ATCC 21993 (in the document also referred to as FERM-P No. 412). The document particularly describes culturing of the bacterial strain under aerobic conditions in a complex liquid medium (culture broth) containing a carbon source, a nitrogen source and inorganic salts. The proteolytic activity present in the culture broth was monitored during cultivation, indicating the amount of neutral protease secreted by the cells into the liquid supernatant. When the maximum activity was reached the culture was harvested and particulate components including bacterial cells were separated from the supernatant by gel filtration, followed by concentration of the filtrate under reduced pressure. Following a not further specified fractionation step with isopropanol, a preparation representing 70% of the total proteolytic activity detected in the culture broth was obtained. Other methods of protease enrichment taught in U.S. Pat. No. 3,930,954 include salting out with ammonium sulfate and precipitation with methanol, ethanol and acetone, each resulting in a crude preparation. Subsequently, further purification steps were applied, ultimately leading to a purified preparation. By way of ultracentrifugation analysis a molecular weight of 35,900 Daltons (Da) was determined, and a number of other biochemical and biophysical parameters were examined. However, no unequivocal data were supplied clarifying whether the disclosed preparation contained a homogeneously purified single protease or a mixture of different proteins.

Stenn, K. S., et al., J. Invest. Dermatol. 93 (1989) 287-290 disclose an analysis of the substrate specificity of a neutral protease (=Dispase®). In addition, a further biochemical characterization of the neutral protease is presented, using purified material derived from the culture filtrate of *B. polymyxa,* and making reference to U.S. Pat. No. 3,930,954. Notably, an SDS PAGE gel representing a sample of 600 µg of protein of a commercially available Dispase® preparation is shown in the document. The Coomassie Blue-stained gel presents a thin major band migrating at 41 kDa, but also at least two faint bands migrating between 30 and 20 kDa, and a further faint band migrating between 20 and 14.4 kDa.

Using *B. polymyxa* strain 72 of Murao, S., et al. (Agric. Biol. Chem. 47 (1979) 941-947) the authors of Takekawa, S., et al., J. Bacteriology 173 (1991) 6820-6825 describe the cloning in *E. coli* of a genomic *B. polymyxa* DNA (SEQ ID NO:1) comprising a nucleotide sequence with an open reading frame apparently encoding the preproenzyme with 590 amino acids (SEQ ID NO:2; primary translation product, precursor molecule prior to secretion) of a neutral protease. Based on the amino acid composition the molecular weight of the conceptual mature (processed) secreted protein comprising 304 amino acids was calculated to be 32,477 Da. Neutral protease expressed in *E. coli* from a genomic *B. polymyxa* fragment and analyzed from the supernatant of disrupted transformed *E. coli* cells was found to migrate at about 35 kDa in SDS PAGE gels.

For comparison, Takekawa, S., et al, (supra) also purified B. polymyxa extracellular neutral protease from culture fluid. The N-terminal amino acid sequence of the purified neutral protease was determined. Notably, the first three amino acid residues in the B. polymyxa N-terminal sequence of Ala Thr Gly Thr Gly Lys Gly Val Len Gly Asp Xaa Lys Ser Phe (SEQ ID NO:4) differ from the predicted amino acid sequence comprised in SEQ ID NO:2 at the positions 287-301 which were found to be Asn Gin Ala Thu Gly Lys Gly Val Len Gly Asp Sec Lys Ser Phe (SEQ ID NO:8). The reason for this discrepancy remained unclear and was not elucidated further.

The authors of the present disclosure set out to produce a transformed microbial host strain recombinantly expressing neutral protease from *Paenibacillus polymyxa.* Unexpectedly it turned out that the sequences disclosed by Takekawa, S., et al. (supra) were not suited to construct a suitable expression strain. Even more surprising, DNA isolated from *B. polymyxa* ATCC 21993 encoded an amino acid sequence of a primary translation product for a neutral protease which not only comprised 592 amino acids but also showed alterations at several position in the encoded polypeptide, when compared with previously published sequences. A further surprising effect was that Bacillus amyloliquefaciens is a particularly suited host organism for recombinant production of the neutral protease originating from Paenibacillus polymyxa.

SUMMARY

A first aspect of all embodiments as disclosed herein is a method for recombinantly producing a neutral protease, the method comprising the steps of (a) providing in an expression vector a DNA with a sequence encoding a preproenzyme according to SEQ ID NO:5, and transforming a host organism with the expression vector, thereby obtaining a transformed host organism, wherein the host organism is a gram-positive prokaryotic species; followed by (b) expressing the DNA in the transformed host organism, wherein the transformed host organism secretes the neutral protease; followed by (c) isolating the secreted neutral protease; thereby recombinantly producing the neutral protease.

A second aspect of all embodiments as disclosed herein is a neutral protease obtained by performing a method for recombinantly producing a neutral protease as disclosed herein.

A third aspect of all embodiments as disclosed herein is a method of isolating living cells from animal tissue in vitro, comprising the steps of (a) providing a recombinantly produced neutral protease obtained by performing a method according to any of the claims 1 to 8, and (b) incubating the tissue in vitro with the neutral protease of step (a), wherein protein components of the extracellular matrix of the tissue are proteolytically degraded, and wherein a layer of cells or a suspension of individual living cells is obtained, thereby isolating living cells from animal tissue in vitro.

A fourth aspect of all embodiments as disclosed herein is the use of a neutral protease obtained by performing a method for recombinantly producing a neutral protease as disclosed herein, the use of the neutral protease being the isolation of living cells from animal tissue in vitro.

A fifth aspect of all embodiments as disclosed herein is a kit of parts comprising in a sealed compartment a lyophilizate of a neutral protease obtained by performing a method for recombinantly producing a neutral protease as disclosed herein.

A sixth aspect of all embodiments as disclosed herein is a method for making a blend of a plurality of proteases, comprising the steps of (a) providing a recombinantly produced neutral protease obtained by performing a method obtained performing a method for recombinantly producing a neutral protease as disclosed herein, and (b) mixing the neutral protease of step (a) with a further protease.

A seventh aspect of all embodiments as disclosed herein is a nucleotide sequence encoding a polypeptide comprising the amino acid sequence of position 289 to position 592 of SEQ ID NO:5, the nucleotide sequence being selected from the group consisting of (a) a nucleotide sequence having the sequence of position 898 to position 1811 in SEQ ID NO:6; (b) nucleotide sequences derived from the nucleotide sequence of position 898 to position 1811 of SEQ ID NO:6 as a result of the degenerated code.

An eighth aspect of all embodiments as disclosed herein is a vector containing a nucleotide sequence as disclosed herein.

A ninth aspect of all embodiments as disclosed herein is a transformed prokaryotic Gram-positive host organism containing at least one vector as disclosed herein.

BRIEF DESCRIPTION OF THE FIGURES

FIG. 1 Alignment of the published amino acid sequence of Takekawa, S., et al., J. Bacteriology 173 (1991) 6820-6825 (SEQ ID NO:3; "Seq-1" in the Figure) with the amino acid sequence originating from P. polymyxa ATCC 21993 (SEQ ID NO:5; "Seq-2" in the Figure), disclosed herein.

DETAILED DESCRIPTION

Dispase® (=neutral protease originating from Paenibacillus polymyxa, P. polymyxa) is a metalloenzyme which is classified as an amino-endo peptidase capable of cleaving fibronectin, collagen IV, and collagen I, but the latter apparently to a lesser extent. P. polymyxa neutral protease is useful for tissue dissociation (=disaggregation) and particularly for subcultivation procedures since it does not damage cell membranes. Since P. polymyxa neutral protease according to the present disclosure can be produced from a bacterial source, it is free of mycoplasma and animal virus contamination. It is very stable with respect to temperature, pH and interference by serum components. P. polymyxa neutral protease activity is greatly reduced by dilution, allowing suspension cultures to grow without difficulty. P. polymyxa neutral protease can even been added to cell suspension cultures to prevent unwanted cell clumping.

P. polymyxa neutral protease prepared recombinantly according to the present disclosure is useful to prepare many types of cells for culture. Thus, P. polymyxa neutral protease as provided herewith is a rapid, effective, but gentle agent for separating even cell layers, that is to say intact epidermis from the dermis and intact epithelial sheets in culture from the substratum. In both cases, it affects separation by cleaving extracellular matrix proteins in the basement membrane zone region while preserving the viability of the epithelial cells. P. polymyxa neutral protease according to the present disclosure and used as sole protease is useful for detaching epidermal cells as confluent, intact sheets from the surface of culture dishes without dissociating the cells. Such a procedure paves the way for the use for culture and even transplantation of skin epithelial cell sheets detached from the culture substrate by P. polymyxa neutral protease. Also, P. polymyxa neutral protease is useful for the harvest and transfer of normal diploid cells and cell lines. Further applications for tissue dissociation make use of blends of P. polymyxa neutral protease and a further protease such as a collagenase.

According to the surprising findings of the authors of the present disclosure, there is provided a method for recombinantly producing a neutral protease, the method comprising the steps of (a) providing in an expression vector a DNA with a sequence encoding a preproenzyme according to SEQ ID NO:5, and transforming a host organism with the expression vector, thereby obtaining a transformed host organism, wherein the host organism is a gram-positive prokaryotic species; followed by (b) expressing the DNA in the transformed host organism, wherein the transformed host organism secretes the neutral protease; followed by (c) isolating the secreted neutral protease; thereby recombinantly producing the neutral protease. More specifically, the DNA sequence originates from Paenibacillus polymyxa ATCC 21993.

The sequence encoding the preproenzyme according to SEQ ID NO:5 can be expressed in any suitable host organism known to the skilled person. A particular host organism is a gram-positive bacterium, specifically a species selected from the group consisting of Bacillus, Clostridium, Lactococcus, Lactobacillus, Staphylococcus and Streptococcus. A very suitable way of recombinantly producing the neutral protease encoded by SEQ ID NO:5 makes use of the species Bacillus amyloliquefaciens as transformed host organism.

In a specific embodiment, the step of expressing the DNA in the transformed host organism is performed by culturing the transformed host organism in a liquid medium, wherein the transformed host organism secretes the neutral protease into the liquid medium. Subsequently, the secreted neutral protease can be isolated from the liquid medium.

Further advantage can be achieved by using in any of the methods for recombinantly producing a neutral protease a host organism which is deficient for extracellular proteases. Examples for B. amyloliquefaciens extracellular proteases are Npr and Apr, well known to the skilled person.

In an exemplary workflow for tissue dissociation, P. polymyxa neutral protease recombinantly produced according to the present disclosure is provided as a lyophilizate. In a first step, the lyophilizate is dissolved in a physiologically suited buffer, e.g. in PBS (phosphate buffered saline) which is free of $Mg^{2+}$ and $Ca^{2+}$ ions. The P. polymyxa neutral protease solution is then sterilized, e.g. by way of filtration through a filter membrane (e.g. 0.22 µm pore size). A sample of living tissue is obtained, i.e. removed from the animal. Alternatively, a culture vessel with adherent cells or a culture vessel with cell aggegates is provided (the cells are also referred to as "tissue" herein). In a particular embodiment, the tissue is fragmented by mechanical means (e.g. using scissors or a scalpel), and the fragments are washed in sterile PBS. Subsequently, the fragments are incubated in pre-warmed P. polymyxa neutral protease solution, whereby the fragments are covered by the solution. Incubation with P. polymyxa neutral protease is typically performed at physiological temperature, particularly at 37° C.

The time needed for the desired (i.e. the degree or extent of) tissue dissociation is usually determined empirically, wherein typically P. polymyxa neutral protease concentration in the solution and/or incubation time are varied. Incubation time in P. polymyxa neutral protease solution can be several hours without adverse effects on the cells. The incubated tissue can optionally be agitated gently. If necessary, dispersed cells can be separated from still existing aggregates by way of passing the obtained cell suspension through a sterile mesh or grid. Decanting is also a method to obtain dissociated cells. Further techniques are known to the skilled person, particularly to remove cell layers which are detached from tissue underneath by incubation with P. polymyxa neutral protease. Fresh Dispase solution may be added if further disaggregation is desired.

Dissociated cells or cell layers can be pelleted, enzyme solution can be removed by decanting, or the P. polymyxa neutral protease solution is diluted with cell culture medium, in order to inhibit further proteolytic activity. Other methods to do so are possible. Cells obtained by the above workflow can be plated and cultured using standard procedures.

Thus, the present disclosure further provides a method to isolate living cells from animal tissue in vitro, comprising the steps of (a) providing a recombinantly produced neutral protease obtained by performing a method according to any of the claims 1 to 8, and (b) incubating the tissue in vitro with the neutral protease of step (a), wherein protein components of the extracellular matrix of the tissue are proteolytically degraded, and wherein a cell layer or a suspension of individual cells is obtained. Specifically, the animal tissue origins from a vertebrate animal, more specifically from an animal species selected from mouse, guinea pig, hamster, rat, dog, sheep, goat, pig, bovine, horse, a primate species, and human.

In another embodiment, a method to isolate living cells from animal tissue in vitro comprises the use of a protease blend which includes a P. polymyxa neutral protease recombinantly produced as disclosed herein. The blend may, by way of example comprise a further neutral protease such as thermolysin. Further, blends of P. polymyxa neutral protease with a collagenase provide great advantage for tissue dissociation.

In a specific embodiment, P. polymyxa neutral protease recombinantly produced as disclosed herein or a blend of proteases including P. polymyxa neutral protease recombinantly produced as disclosed herein is provided as a lyophilizate, i.e. as a freeze-dried preparation. Such a preparation can be stored for an extended amount of time.

Further, there is provided a kit of parts comprising in a sealed compartment, such as a bottle, a lyophilizate of a neutral protease obtained by performing a method for recombinantly producing a neutral protease, as disclosed herein. The kit may contain in a separate sealed compartment a lyophilized preparation of a collagenase. The kit may also contain in a separate sealed compartment a lyophilized preparation of a thermolysin. Another embodiment is a kit comprising in a sealed compartment, such as a bottle, a lyophilizate of a neutral protease obtained by performing a method for recombinantly producing a neutral protease, as disclosed herein, wherein the neutral protease is blended with a further protease such as (but not limited to) a collagenase and/or thermolysin.

The following examples and the sequence listing are provided to aid the understanding of the present invention, the true scope of which is set forth in the appended claims. It is understood that modifications can be made in the procedures set forth without departing from the spirit of the teachings disclosed herein.

EXAMPLE 1

Construction of Expression Constructs (DNA)

Using the polymerase chain reaction (PCR) and several synthesized single- and/or double-stranded DNA oligonucleotides representing subsequences of the desired coding and non-coding genomic DNA strands, artificial gene sequences were generated. To start with, partially overlapping pairs of oligonucleotides representing fragments of opposite strands were hybridized with template DNA, and double-stranded DNA molecules were generated by polymerase-mediated strand-extension, and subsequent PCR amplification. Further DNA molecules were created synthetically. All sequences of artificially generated DNAs were verified by sequencing.

EXAMPLE 2

Expression Constructs Using Published Sequence Information

A first attempt to express P. poymyxa neutral protease was based on the disclosure of Takekawa, S., et al., J. Bacteriology 173 (1991) 6820-6825. In a first step, the nucleotide sequence of SEQ ID NO:1, specifically the subsequence of CDS (343) . . . (2115) corresponding to the open reading frame encoding SEQ ID NO:2 was adapted by changing the codon usage. While the encoded amino acid sequence remained unchanged, neutral mutations optimizing the open reading frame for expression in *Bacillus subtilis* were introduced. An artificial DNA with the reading frame encoding SEQ ID NO:2 was created and synthesized. It encoded the P. polymyxa amino acid sequence of the preproenzyme with 590 amino acids, i.e. including the signal sequence and the propeptide. In the expression construct a *B. subtilis*-specific ribosome binding site was introduced upstream of the open reading frame. The DNA construct was cloned in an expression vector which provides a growth phase-specific promoter driving transcription in *B. subtilis* in the stationary phase of growth in liquid culture. The resulting selectable and replication-competent expression plasmid was pLE2D01nprPp.

A derivative was constructed by fusing three Glycines and six Histidines to the C-terminus of the amino acid sequence of the preproenzyme resulting in an encoded polypeptide with 599 amino acids with six terminal Histidines. The resulting selectable and replication-competent expression plasmid was pLE2D01nprHisPp.

Transformed *B. subtilis* strains were generated and expression experiments under standard conditions were made; i.e. conditions were applied in case of other expression targets have shown to be permissive with expression and secretion of detectable quantities of target protein.

Surprisingly, both expression plasmids, pLE2D01nprPp and pLE2D01nprHisPp, lead to negative results. Both attempts to express and secrete P. polymyxa neutral protease were unsuccessful.

To exclude any negative impact of the promoter sequence, although such an effect was thought unlikely, the promoter in each of the two above plasmids was exchanged by another promoter driving expression dependent on the addition of a specific inductor compound to the culture. The resulting expression plasmids were designated pLE2E01nprPp and pLE2E01nprHisPp. Expression experiments were made including the step of addition of the inductor. As a result, these modifications did not lead to a change. Both further attempts to express and secrete *P. polymyxa* neutral protease were unsuccessful.

In a further attempt, the *B. subtilis* specific ribosome binding site was exchanged by the native *P. polymyxa* ribosome binding site of the originally described gene (SEQ ID NO:1). The resulting expression plasmids were designated pLE2D01nprRBSPp and pLE2D01nprRBSHisPp. Again, the negative results could not be reversed. Both additional attempts to express and secrete *P. polymyxa* neutral protease were unsuccessful.

In addition, mutation experiments were made altering/deleting amino acid positions relating to the sequence discrepancy shown in SEQ ID NO:3, i.e. by the N-terminal amino acid sequence of the native neutral protease isolated from *Paenibacillus polymyxa* culture supernatant.

Surprisingly and unexpectedly, none of the above straightforward attempts to express *P. polymyxa* neutral protease in *Bacillus subtilis* lead to protease activity which was above background, compared to a *B. subtilis* control strain transformed with an "empty" expression vector, i.e. with a vector comprising the same features as described above but without any inserted desired coding sequence. Identical results were obtained, when *B. amyloliquefaciens* was used as expression host.

It is noted in this regard that the sequences published by Takekawa, S., et al., J. Bacteriology 173 (1991) 6820-6825 were cloned and selected in *E. coli,* that is to say in a microbial organism which was unrelated to *P. polymyxa,* taxonomically and in evolutionary terms. One may speculate that passage though such a distinct host might have lead to alterations of the foreign DNA. Also, Takekawa, S., et al. (supra) characterized neutral protease expression in *E. coli* using cellular extracts. However, positive clones were initially identified based on a halo on skim milk agar plates, hinting at some extracellular protease activity at an initial phase of the study.

The exact reason has not been found to explain why the published sequence of Takekawa, S., et al. (supra) does not lead to detectable expression of neutral protease, at least as far as the *B. subtilis* system is concerned. Nevertheless, a further attempt was made to elucidate whether the sequence information documented by Takekawa S. et al. (supra) might not represent the true Paenibacillus polymyxa gene.

EXAMPLE 3

Sequencing Results for *Paenibacillus Polymyxa* Strain ATCC 21993

Total genomic DNA isolated from *Paenibacillus polymyxa* strain ATCC 21993 was isolated and the gene encoding the neutral protease was amplified using PCR. The amplified DNA was sequenced. Surprisingly, several differences on the DNA sequence level were found, the differences giving rise to changes in the amino acid sequence which is encoded. The amino acid sequence of the neutral protease gene of the ATCC 21993 strain is given in SEQ ID NO:5.

On the amino acid sequence level an alignment with the published sequence of Takekawa, S., et al. (supra) is presented in FIG. 1. The alignment shows a number of amino acid exchanges and even a deletion and an insertion. 17 of the amino acid exchanges could be of higher-order structural relevance since in these cases the amino acids are not similar (size, charge) but differ significantly.

Notably, the amino acid sequence determined in the present study contained the N-terminus determined earlier by Takegawa S.et al. (supra). Thus positions 289 to 303 of SEQ ID NO:5 correspond to the previously determined N-terminal sequence of SEQ ID NO:4. According to the present sequencing data, following a proteolytic maturation process including N-terminal proteolytic processing during the course of secretion, the extracellular neutral protease derived from the ATCC 21993 strain is the polypeptide given by the amino acid sequence of SEQ ID NO:5 from position 289 to position 592.

EXAMPLE 4

Expression Constructs Using Published Sequence Information

The DNA encoding the neutral protease was isolated from Paenibacillus polymyxa strain ATCC 21993 as described in Example 3. Based on the amino acid sequence of SEQ ID NO:5 a DNA sequence for expression in B. subtilis encoding the neutral protease was devised and cloned in different expression vectors, in analogy to Example 2. The DNA sequence of a cloned fragment including the coding sequence of the of the neutral protease (preproenzyme) of said *Paenibacillus polymyxa* strain ATCC 21993 is presented as SEQ ID NO:6. An exemplary construct encoded the *P. polymyxa* amino acid sequence of the preproenzyme including the signal sequence and the propeptide. The DNA construct was cloned in an expression vector which provides a growth phase-specific promoter driving transcription in *B. subtilis* in the stationary phase of growth in liquid culture. The resulting selectable and replication-competent expression plasmid was pLE2D01DisnatPp.

It was further attempted to construct a derivative by fusing a tag sequence of three consecutive Glycines followed by six Histidines to the C-terminus of the amino acid sequence of the preproenzyme. Respective transformation experiments yielded clones which on milk agar plates produced halos indicative of protease secretion. Thus, recombinant production of the neutral protease is possible in *B. subtilis*.

Transformed *B. subtilis* strains were characterized further. Sequencing of expression plasmids surprisingly revealed that all these clones contained neutral protease-specific open reading frames in which the added Histidine tag was lost. In the particular *B. subtilis* expression system the His-tag structure appended to the C-terminus could have been incompatible with expression and/or secretion of the proteolytically active recombinant neutral protease enzyme. Thus, this attempt was not pursued further and no clones actively expressing a recombinant His-tagged neutral protease were generated in the *B. subtilis* system.

However, the expression plasmid pLE2D01DisnatPp was transformed into several *Bacillus* species, including not only *Bacillus subtilis* but also *Bacillus amyloliquefaciens*. Control transformations were made with "empty" expression vectors, as described before.

Surprisingly, in liquid cultures transformed *Bacillus amyloliquefaciens* host strains secreted particularly high amounts of neutral protease into the medium while under the same conditions no significant neutral protease activities in the culture supernatant were observed with *Bacillus subtilis*. The effect did not seem to be dependent on the composition of the liquid medium. The reason for this unexpected observation was not elucidated.

Particular transformed *Bacillus subtilis* host strains used for transformation contained loss-of-function mutations in one or more endogenous genes encoding an extracellular (secreted) protease. Such strains are considered to be advantageous, particularly in the present case when the desired target protein to be recombinantly expressed and secreted is a protease itself. Particularly in the transformed *B. subtilis* host protease genes selected from AprE, NprE, Epr, and a combination thereof were mutated. In addition, strains were obtained in which all three of these genes were mutated.

With respect to *Bacillus amyloliquefaciens*, advantageous mutations in the host strain included the endogenous extracellular protease genes Npr and Apr. Respective transformants werde generated including one or both of the two aforementioned protease loss-of-function mutations.

EXAMPLE 5

Determination of Proteolytic Activity in Liquid Medium

The EnzChek® Protease Assay Kits were used (Invitrogen, E6638). The direct fluorescence-based assay detects metallo-, serine, acid and sulfhydryl proteases. The assay kit contains casein derivatives that are labeled with the pH-insensitive greenfluorescent BODIPY® FL (E6638) dye, resulting in almost total quenching of the conjugate's fluorescence. Protease-catalyzed hydrolysis releases fluorescent BODIPY FL dye—labeled peptides. The accompanying increase in fluorescence, which can be measured with a spectrofluorometer, minifluorometer or microplate reader, is proportional to protease activity.

Control experiments were made with samples in which no neutral protease was expressed ("null samples"). Additional controls were made with samples, including "null samples" to which a pre-determined amount of commercially available neutral protease (Dispase®, Roche Diagnostics Manheim, Germany, Cat. No. 04942086001) was added.

The invention claimed is:

1. A method for making a blend of a plurality of proteases, comprising the steps of
   (a) transforming a host organism with an expression vector comprising a nucleic acid sequence encoding a neutral protease comprising the amino acid sequence of SEQ ID NO: 5, thereby obtaining a transformed host organism, wherein the host organism is a gram-positive prokaryotic species;
   (b) culturing the transformed host organism in a culture medium, wherein the transformed host organism secretes the neutral protease into the culture medium;
   (c) isolating the secreted neutral protease; and
   (d) mixing the isolated neutral protease provided in step (c) with an additional protease;
   thereby making a blend of a plurality of proteases.

2. The method according to claim 1, wherein the additional protease is selected from the group consisting of a collagenase and a thermolysin.

3. A method for recombinantly producing a neutral protease, the method comprising the steps of
   (a) providing an expression vector comprising a DNA with a nucleotide sequence encoding a neutral protease comprising the amino acid sequence of SEQ ID NO: 5;
   (b) transforming a host organism of the species *Bacillus amyloliquefaciens* with the expression vector, thereby obtaining a transformed host organism;

(c) culturing the transformed host organism in a culture medium, wherein the transformed host organism secretes the neutral protease into the culture medium; and (d) isolating the secreted neutral protease;

thereby recombinantly producing the neutral protease.

4. The method according to claim 3, wherein the nucleotide sequence of the DNA comprises the sequence of position 34 to position 1896 of SEQ ID NO: 6.

5. The method according to claim 3, wherein the culture medium is a liquid medium.

6. The method according to claim 5, wherein step (d) comprises isolating the secreted neutral protease from the liquid medium.

7. The method according to claim 3, wherein the host organism is deficient of an extracellular protease selected from Npr and Apr.

* * * * *

SEQUENCE LISTING

```
<160> NUMBER OF SEQ ID NOS: 8

<210> SEQ ID NO 1
<211> LENGTH: 2418
<212> TYPE: DNA
<213> ORGANISM: Bacillus polymyxa 72
<220> FEATURE:
<221> NAME/KEY: misc_feature
<223> OTHER INFORMATION: Paenibacillus polymyxa npr gene for
      extracellular neutral protease, "extracellular neutral protease"
      genomic sequence disclosed by Takekawa, S., Uozumi, N.,
      Tsukagoshi, N. and Udaka, S. (J. Bacteriol. 172 (21), 6820-6825
      (1991)) Genbank: D00861.1
<220> FEATURE:
<221> NAME/KEY: CDS
<222> LOCATION: (343)..(2115)

<400> SEQUENCE: 1
gatcttctcg tccgtcattc tctgtgctaa tatcagagcc agatgatggg agttcgaaaa      60
atcatctttt gttttttttg cataaggcaa cttttttcca ttatccgctt ttatccacta     120 tcttttata cgacaggaag ggagggggttt gttaccttt taggctactt gcttcaaatg      180
cagtaccctt ttttcacgca cgcttcatga aaaacacttc ggtatttctc ttcatgttcc     240
attcttctat tccagacgac aacacgacct acataaatgg cgtaatgcct tattcaaagc     300
aggataattc gtcctgacat taatcgagga gagtgaattt tt atg aaa aaa gta       354
                                              Met Lys Lys Val
                                                1 tgg ttt tcg ctt ctt gga gga gct atg tta tta ggg tct gtg gcg tct      402
Trp Phe Ser Leu Leu Gly Gly Ala Met Leu Leu Gly Ser Val Ala Ser
 5                  10                  15                  20
```

-continued

| | |
|---|---|
| ggt gca tct gcg gag agt tcc gtt tcg gga cca gca cag ctt aca ccg<br>Gly Ala Ser Ala Glu Ser Ser Val Ser Gly Pro Ala Gln Leu Thr Pro<br>                25                              30                          35 | 450 |
| acc ttc cac acc gag caa tgg aaa gct cct tcc tcg gta tca ggg gac<br>Thr Phe His Thr Glu Gln Trp Lys Ala Pro Ser Ser Val Ser Gly Asp<br>                40                            45                          50 | 498 |
| gac att gta tgg agc tat ttg aat cga caa aag aaa tcg tta ctg ggt<br>Asp Ile Val Trp Ser Tyr Leu Asn Arg Gln Lys Lys Ser Leu Leu Gly<br>                55                            60                          65 | 546 |
| gtg gat agc tcc agt gta cgt gaa caa ttc cga atc gtt gat cgc aca<br>Val Asp Ser Ser Ser Val Arg Glu Gln Phe Arg Ile Val Asp Arg Thr<br>70                            75                            80 | 594 |
| agc gac aag tcc ggt gtg agc cat tat cga ctg aag cag tat gta aac<br>Ser Asp Lys Ser Gly Val Ser His Tyr Arg Leu Lys Gln Tyr Val Asn<br>85                            90                            95                         100 | 642 |
| ggg att ccc gta tat gga gct gag caa act att cat gtg ggc aaa tct<br>Gly Ile Pro Val Tyr Gly Ala Glu Gln Thr Ile His Val Gly Lys Ser<br>                          105                             110                         115 | 690 |
| ggt gag gtc acc tct tac tta gga gcg gtg att aat gag gat cag cag<br>Gly Glu Val Thr Ser Tyr Leu Gly Ala Val Ile Asn Glu Asp Gln Gln<br>                120                            125                         130 | 738 |
| gaa gaa gct acg caa ggt aca act cca aaa atc agc gct tct gaa gcg<br>Glu Glu Ala Thr Gln Gly Thr Thr Pro Lys Ile Ser Ala Ser Glu Ala<br>        135                            140                         145 | 786 |
| gtt tac acc gca tat aaa gaa gca gct gca cgt att gaa gcc ctc cct<br>Val Tyr Thr Ala Tyr Lys Glu Ala Ala Ala Arg Ile Glu Ala Leu Pro<br>        150                            155                         160 | 834 |
| acc tcc gac gat act att tct aaa gac gct gag gag cca agc agt gta<br>Thr Ser Asp Asp Thr Ile Ser Lys Asp Ala Glu Glu Pro Ser Ser Val<br>165                            170                            175                         180 | 882 |
| agt aaa gat act tac gcc gaa gca gct aac aac gac aaa acg ctt tct<br>Ser Lys Asp Thr Tyr Ala Glu Ala Ala Asn Asn Asp Lys Thr Leu Ser<br>                185                            190                         195 | 930 |
| gtt gat aag gac gag ctg agt ctt gat aag gca tct gtc ctg aaa gat<br>Val Asp Lys Asp Glu Leu Ser Leu Asp Lys Ala Ser Val Leu Lys Asp<br>        200                            205                         210 | 978 |
| agc aaa att gaa gca gtg gag gcc gaa aaa agt tcc att gcc aaa atc<br>Ser Lys Ile Glu Ala Val Glu Ala Glu Lys Ser Ser Ile Ala Lys Ile<br>                215                            220                         225 | 1026 |
| gct aat cta cag cct gaa gta gat cct aaa gca gaa ctc tac tac tac<br>Ala Asn Leu Gln Pro Glu Val Asp Pro Lys Ala Glu Leu Tyr Tyr Tyr<br>        230                            235                         240 | 1074 |
| cct aaa ggg gat gac ctg ctg cta gtt tat gtg aca gaa gtt aat gtt<br>Pro Lys Gly Asp Asp Leu Leu Leu Val Tyr Val Thr Glu Val Asn Val<br>245                            250                            255                         260 | 1122 |
| tta gaa cct gcc cca ctg cgt acc cgc tac att att gat gcc aat gac<br>Leu Glu Pro Ala Pro Leu Arg Thr Arg Tyr Ile Ile Asp Ala Asn Asp<br>                  265                            270                         275 | 1170 |
| ggc agc atc gta ttc cag tat gac atc att aat gaa gcg aca ggt aaa<br>Gly Ser Ile Val Phe Gln Tyr Asp Ile Ile Asn Glu Ala Thr Gly Lys<br>                      280                            285                         290 | 1218 |
| ggt gtg ctt ggt gat tcc aaa tcg ttc act act acc gct tcc ggc agt<br>Gly Val Leu Gly Asp Ser Lys Ser Phe Thr Thr Thr Ala Ser Gly Ser<br>                295                            300                         305 | 1266 |
| agc tac cag tta aaa gat acc aca cgc ggt aac ggt atc gtg act tac<br>Ser Tyr Gln Leu Lys Asp Thr Thr Arg Gly Asn Gly Ile Val Thr Tyr<br>        310                            315                         320 | 1314 |
| acg gcc tcc aac cgc caa agc atc cca ggc acc ctt ttg aca gat gct<br>Thr Ala Ser Asn Arg Gln Ser Ile Pro Gly Thr Leu Leu Thr Asp Ala<br>325                            330                            335                         340 | 1362 |

```
gat aat gta tgg aat gat cca gcc ggt gtg gat gcc cat gcg tat gct      1410
Asp Asn Val Trp Asn Asp Pro Ala Gly Val Asp Ala His Ala Tyr Ala
            345                 350                 355 gcc aaa acc tat gat tac tat aaa tcc aaa ttt gga cgc aac agc att      1458
Ala Lys Thr Tyr Asp Tyr Tyr Lys Ser Lys Phe Gly Arg Asn Ser Ile
        360                 365                 370 gac gga cgt ggt ctg caa ctc cgt tcg aca gtc cat tac ggc agc cgc      1506
Asp Gly Arg Gly Leu Gln Leu Arg Ser Thr Val His Tyr Gly Ser Arg
    375                 380                 385 tac aac aac gct ttc tgg aac ggc tcc caa atg act tat gga gat gga      1554
Tyr Asn Asn Ala Phe Trp Asn Gly Ser Gln Met Thr Tyr Gly Asp Gly
390                 395                 400 gat gga gac ggt agc aca ttt atc gcc ttc agc ggg gac ccc gat gta      1602
Asp Gly Asp Gly Ser Thr Phe Ile Ala Phe Ser Gly Asp Pro Asp Val
405                 410                 415                 420 gta ggg cat gaa ctt aca cat ggt gtc aca gag tat act tcg aat ttg      1650
Val Gly His Glu Leu Thr His Gly Val Thr Glu Tyr Thr Ser Asn Leu
            425                 430                 435 gaa tat tac gga gag tcc ggc gca ttg aat gag gct ttc tcg gac gtt      1698
Glu Tyr Tyr Gly Glu Ser Gly Ala Leu Asn Glu Ala Phe Ser Asp Val
        440                 445                 450 atc ggt aat gac att caa cgc aaa aac tgg ctt gta ggc gat gat att      1746
Ile Gly Asn Asp Ile Gln Arg Lys Asn Trp Leu Val Gly Asp Asp Ile
    455                 460                 465 tat acg cca aac att tgc ggc gat gcc ctt cgc tca atg tcc aat cct      1794
Tyr Thr Pro Asn Ile Cys Gly Asp Ala Leu Arg Ser Met Ser Asn Pro
470                 475                 480 act ctg tac gat caa cca cat cac tat tcc aac ctg tat aaa ggc agc      1842
Thr Leu Tyr Asp Gln Pro His His Tyr Ser Asn Leu Tyr Lys Gly Ser
485                 490                 495                 500 tcc gat aac ggc ggc gtt cat aca aac agc ggt att atc aat aaa gcc      1890
Ser Asp Asn Gly Gly Val His Thr Asn Ser Gly Ile Ile Asn Lys Ala
            505                 510                 515 tac tac ttg ttg gca caa ggc ggt act ttc cat ggc gtt act gta aat      1938
Tyr Tyr Leu Leu Ala Gln Gly Gly Thr Phe His Gly Val Thr Val Asn
        520                 525                 530 gga att ggg cgc gat gct gcg gtg caa att tat tat agt gcc ttt acg      1986
Gly Ile Gly Arg Asp Ala Ala Val Gln Ile Tyr Tyr Ser Ala Phe Thr
    535                 540                 545 aac tac ctg act tct tct tcc gac ttc tcc aac gca cgt gct gct gtg      2034
Asn Tyr Leu Thr Ser Ser Ser Asp Phe Ser Asn Ala Arg Ala Ala Val
550                 555                 560 atc caa gcc gca aaa gat ctg tac ggg gcg aac tca gca gaa gca act      2082
Ile Gln Ala Ala Lys Asp Leu Tyr Gly Ala Asn Ser Ala Glu Ala Thr
565                 570                 575                 580 gca gct gcc aag tct ttt gac gct gta ggc taa actaaatcat atacgcgatc   2135
Ala Ala Ala Lys Ser Phe Asp Ala Val Gly
            585                 590 ctcctcattt tctgtccata gacctttgcc attgtgcaac tgtcacttgg ctctgccata   2195
ccatggacga aaataggggg tgcagtgtac aagtctgcac cccttccccc cttatttatg   2255
gcgccccctc aaagggctcc ttttctctta taaaagtaat cctgtatctc ttgcttttg   2315 cacagcttct tctcgattgt tgactccagc ttgacataga gagtggaggc gaattcttac   2375
tgtccgtgga taggtaagtt ctcagaattg tttatacgtt ctg                    2418
```

<210> SEQ ID NO 2
<211> LENGTH: 590
<212> TYPE: PRT
<213> ORGANISM: Bacillus polymyxa 72

<400> SEQUENCE: 2

```
Met Lys Lys Val Trp Phe Ser Leu Leu Gly Ala Met Leu Leu Gly
1               5                   10                  15

Ser Val Ala Ser Gly Ala Ser Ala Glu Ser Ser Val Ser Gly Pro Ala
            20                  25                  30

Gln Leu Thr Pro Thr Phe His Thr Glu Gln Trp Lys Ala Pro Ser Ser
            35                  40                  45

Val Ser Gly Asp Asp Ile Val Trp Ser Tyr Leu Asn Arg Gln Lys Lys
        50                  55                  60

Ser Leu Leu Gly Val Asp Ser Ser Val Arg Glu Gln Phe Arg Ile
65                  70                  75                  80

Val Asp Arg Thr Ser Asp Lys Ser Gly Val Ser His Tyr Arg Leu Lys
                85                  90                  95

Gln Tyr Val Asn Gly Ile Pro Val Tyr Gly Ala Glu Gln Thr Ile His
            100                 105                 110

Val Gly Lys Ser Gly Glu Val Thr Ser Tyr Leu Gly Ala Val Ile Asn
        115                 120                 125

Glu Asp Gln Gln Glu Glu Ala Thr Gln Gly Thr Thr Pro Lys Ile Ser
130                 135                 140

Ala Ser Glu Ala Val Tyr Thr Ala Tyr Lys Glu Ala Ala Arg Ile
145                 150                 155                 160

Glu Ala Leu Pro Thr Ser Asp Asp Thr Ile Ser Lys Asp Ala Glu Glu
                165                 170                 175

Pro Ser Ser Val Ser Lys Asp Thr Tyr Ala Glu Ala Asn Asn Asp
            180                 185                 190

Lys Thr Leu Ser Val Asp Lys Asp Glu Leu Ser Leu Asp Lys Ala Ser
        195                 200                 205

Val Leu Lys Asp Ser Lys Ile Glu Ala Val Glu Ala Glu Lys Ser Ser
210                 215                 220

Ile Ala Lys Ile Ala Asn Leu Gln Pro Glu Val Asp Pro Lys Ala Glu
225                 230                 235                 240

Leu Tyr Tyr Tyr Pro Lys Gly Asp Asp Leu Leu Leu Val Tyr Val Thr
                245                 250                 255

Glu Val Asn Val Leu Glu Pro Ala Pro Leu Arg Thr Arg Tyr Ile Ile
            260                 265                 270

Asp Ala Asn Asp Gly Ser Ile Val Phe Gln Tyr Asp Ile Ile Asn Glu
        275                 280                 285

Ala Thr Gly Lys Gly Val Leu Gly Asp Ser Lys Ser Phe Thr Thr Thr
290                 295                 300

Ala Ser Gly Ser Ser Tyr Gln Leu Lys Asp Thr Thr Arg Gly Asn Gly
305                 310                 315                 320

Ile Val Thr Tyr Thr Ala Ser Asn Arg Gln Ser Ile Pro Gly Thr Leu
                325                 330                 335

Leu Thr Asp Ala Asp Asn Val Trp Asn Asp Pro Ala Gly Val Asp Ala
            340                 345                 350

His Ala Tyr Ala Ala Lys Thr Tyr Asp Tyr Tyr Lys Ser Lys Phe Gly
        355                 360                 365

Arg Asn Ser Ile Asp Gly Arg Gly Leu Gln Leu Arg Ser Thr Val His
370                 375                 380

Tyr Gly Ser Arg Tyr Asn Asn Ala Phe Trp Asn Gly Ser Gln Met Thr
385                 390                 395                 400

Tyr Gly Asp Gly Asp Gly Asp Gly Ser Thr Phe Ile Ala Phe Ser Gly
                405                 410                 415
```

-continued

```
Asp Pro Asp Val Val Gly His Glu Leu Thr His Gly Val Thr Glu Tyr
            420                 425                 430

Thr Ser Asn Leu Glu Tyr Tyr Gly Glu Ser Gly Ala Leu Asn Glu Ala
        435                 440                 445

Phe Ser Asp Val Ile Gly Asn Asp Ile Gln Arg Lys Asn Trp Leu Val
    450                 455                 460

Gly Asp Asp Ile Tyr Thr Pro Asn Ile Cys Gly Asp Ala Leu Arg Ser
465                 470                 475                 480

Met Ser Asn Pro Thr Leu Tyr Asp Gln Pro His His Tyr Ser Asn Leu
                485                 490                 495

Tyr Lys Gly Ser Ser Asp Asn Gly Gly Val His Thr Asn Ser Gly Ile
            500                 505                 510

Ile Asn Lys Ala Tyr Tyr Leu Leu Ala Gln Gly Gly Thr Phe His Gly
        515                 520                 525

Val Thr Val Asn Gly Ile Gly Arg Asp Ala Ala Val Gln Ile Tyr Tyr
    530                 535                 540

Ser Ala Phe Thr Asn Tyr Leu Thr Ser Ser Asp Phe Ser Asn Ala
545                 550                 555                 560

Arg Ala Ala Val Ile Gln Ala Ala Lys Asp Leu Tyr Gly Ala Asn Ser
                565                 570                 575

Ala Glu Ala Thr Ala Ala Ala Lys Ser Phe Asp Ala Val Gly
            580                 585                 590

<210> SEQ ID NO 3
<211> LENGTH: 590
<212> TYPE: PRT
<213> ORGANISM: Bacillus polymyxa 72
<220> FEATURE:
<221> NAME/KEY: MISC_FEATURE
<223> OTHER INFORMATION: preproenzyme with 590 amino acids according to
      Takekawa S. et al. J. Bacteriology 173 (1991) 6820-6825

<400> SEQUENCE: 3

Met Lys Lys Val Trp Phe Ser Leu Leu Gly Gly Ala Met Leu Leu Gly
1               5                   10                  15

Ser Val Ala Ser Gly Ala Ser Ala Glu Ser Ser Val Ser Gly Pro Ala
            20                  25                  30

Gln Leu Thr Pro Thr Phe His Thr Glu Gln Trp Lys Ala Pro Ser Ser
        35                  40                  45

Val Ser Gly Asp Asp Ile Val Trp Ser Tyr Leu Asn Arg Gln Lys Lys
    50                  55                  60

Ser Leu Leu Gly Val Asp Ser Ser Val Arg Glu Gln Phe Arg Ile
65                  70                  75                  80

Val Asp Arg Thr Ser Asp Lys Ser Gly Val Ser His Tyr Arg Leu Lys
                85                  90                  95

Gln Tyr Val Asn Gly Ile Pro Val Tyr Gly Ala Glu Gln Thr Ile His
            100                 105                 110

Val Gly Lys Ser Gly Glu Val Thr Ser Tyr Leu Gly Ala Val Ile Asn
        115                 120                 125

Glu Asp Gln Gln Glu Ala Thr Gln Gly Thr Thr Pro Lys Ile Ser
    130                 135                 140

Ala Ser Glu Ala Val Tyr Thr Ala Tyr Lys Glu Ala Ala Arg Ile
145                 150                 155                 160

Glu Ala Leu Pro Thr Ser Asp Asp Thr Ile Ser Lys Asp Ala Glu Glu
                165                 170                 175
```

```
Pro Ser Ser Val Ser Lys Asp Thr Tyr Ala Glu Ala Asn Asn Asp
            180                 185                 190
Lys Thr Leu Ser Val Asp Lys Asp Glu Leu Ser Leu Asp Lys Ala Ser
            195                 200                 205
Val Leu Lys Asp Ser Lys Ile Glu Ala Val Glu Ala Glu Lys Ser Ser
            210                 215                 220
Ile Ala Lys Ile Ala Asn Leu Gln Pro Glu Val Asp Pro Lys Ala Glu
225                 230                 235                 240
Leu Tyr Tyr Tyr Pro Lys Gly Asp Asp Leu Leu Val Tyr Val Thr
            245                 250                 255
Glu Val Asn Val Leu Glu Pro Ala Pro Leu Arg Thr Arg Tyr Ile Ile
            260                 265                 270
Asp Ala Asn Asp Gly Ser Ile Val Phe Gln Tyr Asp Ile Ile Asn Glu
            275                 280                 285
Ala Thr Gly Lys Gly Val Leu Gly Asp Ser Lys Ser Phe Thr Thr Thr
            290                 295                 300
Ala Ser Gly Ser Ser Tyr Gln Leu Lys Asp Thr Thr Arg Gly Asn Gly
305                 310                 315                 320
Ile Val Thr Tyr Thr Ala Ser Asn Arg Gln Ser Ile Pro Gly Thr Leu
            325                 330                 335
Leu Thr Asp Ala Asp Asn Val Trp Asn Asp Pro Ala Gly Val Asp Ala
            340                 345                 350
His Ala Tyr Ala Ala Lys Thr Tyr Asp Tyr Lys Ser Lys Phe Gly
            355                 360                 365
Arg Asn Ser Ile Asp Gly Arg Gly Leu Gln Leu Arg Ser Thr Val His
            370                 375                 380
Tyr Gly Ser Arg Tyr Asn Asn Ala Phe Trp Asn Gly Ser Gln Met Thr
385                 390                 395                 400
Tyr Gly Asp Gly Asp Gly Asp Gly Ser Thr Phe Ile Ala Phe Ser Gly
            405                 410                 415
Asp Pro Asp Val Val Gly His Glu Leu Thr His Gly Val Thr Glu Tyr
            420                 425                 430
Thr Ser Asn Leu Glu Tyr Tyr Gly Glu Ser Gly Ala Leu Asn Glu Ala
            435                 440                 445
Phe Ser Asp Val Ile Gly Asn Asp Ile Gln Arg Lys Asn Trp Leu Val
            450                 455                 460
Gly Asp Asp Ile Tyr Thr Pro Asn Ile Cys Gly Asp Ala Leu Arg Ser
465                 470                 475                 480
Met Ser Asn Pro Thr Leu Tyr Asp Gln Pro His His Tyr Ser Asn Leu
            485                 490                 495
Tyr Lys Gly Ser Ser Asp Asn Gly Gly Val His Thr Asn Ser Gly Ile
            500                 505                 510
Ile Asn Lys Ala Tyr Tyr Leu Leu Ala Gln Gly Gly Thr Phe His Gly
            515                 520                 525
Val Thr Val Asn Gly Ile Gly Arg Asp Ala Ala Val Gln Ile Tyr Tyr
            530                 535                 540
Ser Ala Phe Thr Asn Tyr Leu Thr Ser Ser Asp Phe Ser Asn Ala
545                 550                 555                 560
Arg Ala Ala Val Ile Gln Ala Lys Asp Leu Tyr Gly Ala Asn Ser
            565                 570                 575
Ala Glu Ala Thr Ala Ala Ala Lys Ser Phe Asp Ala Val Gly
            580                 585                 590
```

```
<210> SEQ ID NO 4
<211> LENGTH: 15
<212> TYPE: PRT
<213> ORGANISM: Bacillus polymyxa 72
<220> FEATURE:
<221> NAME/KEY: MISC_FEATURE
<223> OTHER INFORMATION: N-terminal amino acid sequence determined by
      Takekawa S. et al. J. Bacteriology 173 (1991) 6820-6825
<220> FEATURE:
<221> NAME/KEY: MISC_FEATURE
<222> LOCATION: (12)..(12)
<223> OTHER INFORMATION: Xaa can be any naturally occurring amino acid

<400> SEQUENCE: 4

Ala Thr Gly Thr Gly Lys Gly Val Leu Gly Asp Xaa Lys Ser Phe
1               5                   10                  15

<210> SEQ ID NO 5
<211> LENGTH: 592
<212> TYPE: PRT
<213> ORGANISM: Paenibacillus polymyxa ATCC21993

<400> SEQUENCE: 5

Met Lys Lys Val Trp Val Ser Leu Leu Gly Ala Met Leu Leu Gly
1               5                   10                  15

Ser Val Ala Ser Gly Ala Ser Ala Glu Ser Ser Val Ser Gly Pro Thr
                20                  25                  30

Gln Leu Thr Pro Thr Phe His Ala Glu Gln Trp Lys Ala Pro Ser Ser
            35                  40                  45

Val Ser Gly Asp Asp Ile Val Trp Ser Tyr Leu Asn Arg Gln Lys Lys
    50                  55                  60

Ser Leu Leu Gly Ala Asp Asp Ser Ser Val Arg Glu Gln Phe Arg Ile
65                  70                  75                  80

Val Asp Arg Thr Ser Asp Lys Ser Gly Val Ser His Tyr Arg Leu Lys
                85                  90                  95

Gln Tyr Val Asn Gly Ile Pro Val Tyr Gly Ala Glu Gln Thr Ile His
            100                 105                 110

Val Gly Lys Ser Gly Glu Val Thr Ser Tyr Leu Gly Ala Val Val Thr
    115                 120                 125

Glu Asp Gln Gln Ala Glu Ala Thr Gln Gly Thr Thr Pro Lys Ile Ser
130                 135                 140

Ala Ser Glu Ala Val Tyr Thr Ala Tyr Lys Glu Ala Ala Arg Ile
145                 150                 155                 160

Glu Ala Leu Pro Thr Ser Asp Asp Thr Ile Ser Lys Asp Val Glu Glu
                165                 170                 175

Gln Ser Ser Val Ser Lys Asp Thr Tyr Ala Glu Ala Ala Asn Asn Glu
            180                 185                 190

Lys Thr Leu Ser Thr Asp Lys Asp Glu Leu Ser Leu Lys Ala Ser
    195                 200                 205

Ala Leu Lys Asp Ser Lys Ile Glu Ala Val Glu Ala Lys Ser Ser
210                 215                 220

Ile Ala Lys Ile Ala Asn Leu Gln Pro Glu Val Asp Pro Lys Ala Asp
225                 230                 235                 240

Leu Tyr Phe Tyr Pro Lys Gly Asp Asp Leu Gln Leu Val Tyr Val Thr
                245                 250                 255

Glu Val Asn Val Leu Glu Pro Ala Pro Leu Arg Thr Arg Tyr Ile Ile
            260                 265                 270

Asp Ala Asn Asp Gly Ser Ile Val Phe Gln Tyr Asp Ile Ile Asn Glu
    275                 280                 285
```

```
Ala Thr Gly Thr Gly Lys Gly Val Leu Gly Asp Thr Lys Ser Phe Thr
    290                 295                 300
Thr Thr Ala Ser Gly Ser Ser Tyr Gln Leu Lys Asp Thr Thr Arg Gly
305                 310                 315                 320
Asn Gly Val Val Thr Tyr Thr Ala Ser Asn Arg Gln Ser Ile Pro Gly
                325                 330                 335
Thr Ile Leu Thr Asp Ala Asp Asn Val Trp Asn Asp Pro Ala Gly Val
            340                 345                 350

Asp Ala His Thr Tyr Ala Ala Lys Thr Tyr Asp Tyr Tyr Lys Ala Lys
        355                 360                 365
Phe Gly Arg Asn Ser Ile Asp Gly Arg Gly Leu Gln Leu Arg Ser Thr
    370                 375                 380
Val His Tyr Gly Ser Arg Tyr Asn Asn Ala Phe Trp Asn Gly Ser Gln
385                 390                 395                 400
Met Thr Tyr Gly Asp Gly Asp Gly Ser Thr Phe Ile Ala Phe Ser Gly
                405                 410                 415
Asp Pro Asp Val Val Gly His Glu Leu Thr His Gly Val Thr Glu Tyr
            420                 425                 430
Thr Ser Asn Leu Glu Tyr Tyr Gly Glu Ser Gly Ala Leu Asn Glu Ala
        435                 440                 445
Phe Ser Asp Val Ile Gly Asn Asp Ile Gln Arg Lys Asn Trp Leu Val
    450                 455                 460
Gly Asp Asp Ile Tyr Thr Pro Asn Ile Ala Gly Asp Ala Leu Arg Ser
465                 470                 475                 480
Met Ser Asn Pro Thr Leu Tyr Asp Gln Pro Asp His Tyr Ser Asn Leu
                485                 490                 495
Tyr Thr Gly Ser Ser Asp Asn Gly Gly Val His Thr Asn Ser Gly Ile
            500                 505                 510
Ile Asn Lys Ala Tyr Tyr Leu Leu Ala Gln Gly Gly Thr Phe His Gly
        515                 520                 525
Val Thr Val Asn Gly Ile Gly Arg Asp Ala Ala Val Gln Ile Tyr Tyr
    530                 535                 540

Ser Ala Phe Thr Asn Tyr Leu Thr Ser Ser Ser Asp Phe Ser Asn Ala
545                 550                 555                 560
Arg Ala Ala Val Ile Gln Ala Ala Lys Asp Gln Tyr Gly Ala Asn Ser
                565                 570                 575
Ala Glu Ala Thr Ala Ala Ala Lys Ser Phe Asp Ala Val Gly Val Asn
            580                 585                 590
```

<210> SEQ ID NO 6
<211> LENGTH: 1898
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA comprising the nucleotide sequence encoding
enzymatically active neutral protease from Paenibacillus polymyxa,
the DNA having engineered termini facilitating cloning steps
<220> FEATURE:
<221> NAME/KEY: misc_recomb
<222> LOCATION: (5)..(11)
<223> OTHER INFORMATION: artificially generated Pae-I restriction
cleavage site “GCATGC”
<220> FEATURE:
<221> NAME/KEY: CDS
<222> LOCATION: (34)..(1812)

<220> FEATURE:
<221> NAME/KEY: misc_recomb
<222> LOCATION: (1891)..(1896)
<223> OTHER INFORMATION: artificially generated Sal-I restriction
      cleavage site "GTCGAC"

<400> SEQUENCE: 6

```
gctcgcatgc caaatgagga gagtgaattt ttg atg aaa aaa gta tgg gtt tcg         54
                                     Met Lys Lys Val Trp Val Ser
                                     1               5 ctt ctt gga gga gct atg tta tta ggg tct gtc gcg tct ggt gca tca         102
Leu Leu Gly Gly Ala Met Leu Leu Gly Ser Val Ala Ser Gly Ala Ser
         10              15                  20 gcg gag agt tcc gtt tcg ggg cca act cag ctt aca ccg acc ttt cac         150
Ala Glu Ser Ser Val Ser Gly Pro Thr Gln Leu Thr Pro Thr Phe His
     25              30                  35 gcc gag caa tgg aaa gcc cct tcc tcg gta tcg ggg gac gac att gta         198
Ala Glu Gln Trp Lys Ala Pro Ser Ser Val Ser Gly Asp Asp Ile Val
 40              45                  50                  55 tgg agc tat ttg aat cgg caa aag aaa tcg tta ctg ggt gcg gac gac         246
Trp Ser Tyr Leu Asn Arg Gln Lys Lys Ser Leu Leu Gly Ala Asp Asp
                 60                  65                  70 tct agt gta cgt gaa caa ttc cga atc gtt gat cgc aca agc gac aag         294
Ser Ser Val Arg Glu Gln Phe Arg Ile Val Asp Arg Thr Ser Asp Lys
         75                  80                  85 tcc ggt gtg agc cat tat cgg ctg aaa cag tat gta aac ggg att ccc         342
Ser Gly Val Ser His Tyr Arg Leu Lys Gln Tyr Val Asn Gly Ile Pro
     90                  95                 100 gta tat gga gct gaa cag act att cat gtg ggc aaa tct ggt gag gtc         390
Val Tyr Gly Ala Glu Gln Thr Ile His Val Gly Lys Ser Gly Glu Val
105                 110                 115 acc tct tac tta gga gcg gtg gtt act gag gat cag caa gct gaa gct         438
Thr Ser Tyr Leu Gly Ala Val Val Thr Glu Asp Gln Gln Ala Glu Ala
120                 125                 130                 135 acg caa ggt aca act cca aaa atc agc gct tct gaa gcg gtc tac act         486
Thr Gln Gly Thr Thr Pro Lys Ile Ser Ala Ser Glu Ala Val Tyr Thr
                140                 145                 150 gca tat aaa gaa gca gct gca cgg att gaa gcc ctc cct acc tcc gac         534
Ala Tyr Lys Glu Ala Ala Ala Arg Ile Glu Ala Leu Pro Thr Ser Asp
        155                 160                 165 gat acg att tct aaa gat gtt gag gaa caa agc agt gta agc aaa gac         582
Asp Thr Ile Ser Lys Asp Val Glu Glu Gln Ser Ser Val Ser Lys Asp
        170                 175                 180 act tac gcc gaa gca gct aac aac gaa aaa acg cta tct act gat aag         630
Thr Tyr Ala Glu Ala Ala Asn Asn Glu Lys Thr Leu Ser Thr Asp Lys
185                 190                 195 gac gag ctg agt ctt gat aaa gca tct gcc ctg aaa gat agc aaa att         678
Asp Glu Leu Ser Leu Asp Lys Ala Ser Ala Leu Lys Asp Ser Lys Ile
200                 205                 210                 215 gaa gcg gtg gaa gca gaa aaa agt tcc att gcc aaa atc gct aat ctg         726
Glu Ala Val Glu Ala Glu Lys Ser Ser Ile Ala Lys Ile Ala Asn Leu
                220                 225                 230 cag cca gaa gta gat cca aaa gcc gat ctg tac ttc tat cct aaa ggg         774
Gln Pro Glu Val Asp Pro Lys Ala Asp Leu Tyr Phe Tyr Pro Lys Gly
            235                 240                 245 gat gac ctg cag ctg gtt tat gta aca gaa gtc aat gtt tta gaa cct         822
Asp Asp Leu Gln Leu Val Tyr Val Thr Glu Val Asn Val Leu Glu Pro
        250                 255                 260 gcc cca ctg cgt act cgc tac att att gat gcc aat gat ggc agc atc         870
Ala Pro Leu Arg Thr Arg Tyr Ile Ile Asp Ala Asn Asp Gly Ser Ile
265                 270                 275
```

```
gta ttc cag tat gac atc att aat gaa gcg aca ggc aca ggt aaa ggt       918
Val Phe Gln Tyr Asp Ile Ile Asn Glu Ala Thr Gly Thr Gly Lys Gly
280                 285                 290                 295 gtg ctt ggt gat acc aaa tca ttc acc aca act gct tcc ggc agt agc       966
Val Leu Gly Asp Thr Lys Ser Phe Thr Thr Thr Ala Ser Gly Ser Ser
                300                 305                 310 tac cag tta aaa gat aca aca cgc ggt aac ggg gtt gtg acc tac acg      1014
Tyr Gln Leu Lys Asp Thr Thr Arg Gly Asn Gly Val Val Thr Tyr Thr
            315                 320                 325 gcc tcc aac cgt caa agc atc cca ggt acc att ctg acc gat gcc gat      1062
Ala Ser Asn Arg Gln Ser Ile Pro Gly Thr Ile Leu Thr Asp Ala Asp
        330                 335                 340 aat gta tgg aat gat cca gcc ggc gtg gat gcc cat acg tat gct gct      1110
Asn Val Trp Asn Asp Pro Ala Gly Val Asp Ala His Thr Tyr Ala Ala
    345                 350                 355 aaa aca tat gat tac tat aag gcc aaa ttt gga cgc aac agc att gac      1158
Lys Thr Tyr Asp Tyr Tyr Lys Ala Lys Phe Gly Arg Asn Ser Ile Asp
360                 365                 370                 375 gga cgc ggg ctg caa ctc cgt tcg aca gtc cat tat ggt agc cgt tac      1206
Gly Arg Gly Leu Gln Leu Arg Ser Thr Val His Tyr Gly Ser Arg Tyr
                380                 385                 390 aac aac gcc ttc tgg aat ggc tcc caa atg act tat gga gac ggg gac      1254
Asn Asn Ala Phe Trp Asn Gly Ser Gln Met Thr Tyr Gly Asp Gly Asp
            395                 400                 405 ggt agc aca ttt atc gca ttc agc ggg gac ccc gat gtg gta ggt cat      1302
Gly Ser Thr Phe Ile Ala Phe Ser Gly Asp Pro Asp Val Val Gly His
        410                 415                 420 gaa ctt acg cac ggt gtc aca gag tat act tcg aat ttg gaa tat tac      1350
Glu Leu Thr His Gly Val Thr Glu Tyr Thr Ser Asn Leu Glu Tyr Tyr
    425                 430                 435 gga gag tcc ggt gca ttg aat gag gct ttc tcg gac gtc atc ggt aat      1398
Gly Glu Ser Gly Ala Leu Asn Glu Ala Phe Ser Asp Val Ile Gly Asn
440                 445                 450                 455 gac att cag cgt aaa aat tgg ctt gta ggc gat gat att tat acg cca      1446
Asp Ile Gln Arg Lys Asn Trp Leu Val Gly Asp Asp Ile Tyr Thr Pro
                460                 465                 470 aac att gca ggc gat gct ctg cgc tct atg tcc aat cct acc ctg tac      1494
Asn Ile Ala Gly Asp Ala Leu Arg Ser Met Ser Asn Pro Thr Leu Tyr
            475                 480                 485 gat caa cca gat cac tat tcc aac ttg tat aca ggc agc tcc gat aac      1542
Asp Gln Pro Asp His Tyr Ser Asn Leu Tyr Thr Gly Ser Ser Asp Asn
        490                 495                 500 ggc ggt gtt cat acg aac agc ggt att atc aat aaa gcc tac tat ctg      1590
Gly Gly Val His Thr Asn Ser Gly Ile Ile Asn Lys Ala Tyr Tyr Leu
    505                 510                 515 tta gca caa ggt ggt act ttc cat ggc gta act gta aat gga att ggc      1638
Leu Ala Gln Gly Gly Thr Phe His Gly Val Thr Val Asn Gly Ile Gly
520                 525                 530                 535 cgc gat gca gcg gtt caa att tac tat agt gcc ttt acg aac tac ctg      1686
Arg Asp Ala Ala Val Gln Ile Tyr Tyr Ser Ala Phe Thr Asn Tyr Leu
                540                 545                 550 act tct tct tcc gac ttc tcc aac gca cgc gct gct gtg atc caa gca      1734
Thr Ser Ser Ser Asp Phe Ser Asn Ala Arg Ala Ala Val Ile Gln Ala
            555                 560                 565 gca aaa gat cag tac ggt gcg aac tca gca gaa gca act gca gct gcc      1782
Ala Lys Asp Gln Tyr Gly Ala Asn Ser Ala Glu Ala Thr Ala Ala Ala
        570                 575                 580 aaa tct ttt gac gct gta ggc gta aac taa atcatataca cgatcctcct        1832
Lys Ser Phe Asp Ala Val Gly Val Asn
585                 590
```

```
cattttctgt ccatagacct ttgccattgt gcaactgtca cttggctctg ccataccagt    1892
cgacgg                                                               1898
```

<210> SEQ ID NO 7
<211> LENGTH: 592
<212> TYPE: PRT
<213> ORGANISM: Artificial Sequence
<220> FEATURE:
<223> OTHER INFORMATION: Synthetic Construct

<400> SEQUENCE: 7

```
Met Lys Lys Val Trp Val Ser Leu Leu Gly Gly Ala Met Leu Leu Gly
1               5                   10                  15

Ser Val Ala Ser Gly Ala Ser Ala Glu Ser Ser Val Ser Gly Pro Thr
            20                  25                  30

Gln Leu Thr Pro Thr Phe His Ala Glu Gln Trp Lys Ala Pro Ser Ser
        35                  40                  45

Val Ser Gly Asp Asp Ile Val Trp Ser Tyr Leu Asn Arg Gln Lys Lys
    50                  55                  60

Ser Leu Leu Gly Ala Asp Asp Ser Ser Val Arg Glu Gln Phe Arg Ile
65                  70                  75                  80

Val Asp Arg Thr Ser Asp Lys Ser Gly Val Ser His Tyr Arg Leu Lys
                85                  90                  95

Gln Tyr Val Asn Gly Ile Pro Val Tyr Gly Ala Glu Gln Thr Ile His
            100                 105                 110

Val Gly Lys Ser Gly Glu Val Thr Ser Tyr Leu Gly Ala Val Val Thr
        115                 120                 125

Glu Asp Gln Gln Ala Glu Ala Thr Gln Gly Thr Thr Pro Lys Ile Ser
    130                 135                 140

Ala Ser Glu Ala Val Tyr Thr Ala Tyr Lys Glu Ala Ala Ala Arg Ile
145                 150                 155                 160

Glu Ala Leu Pro Thr Ser Asp Asp Thr Ile Ser Lys Asp Val Glu Glu
                165                 170                 175

Gln Ser Ser Val Ser Lys Asp Thr Tyr Ala Glu Ala Ala Asn Asn Glu
            180                 185                 190

Lys Thr Leu Ser Thr Asp Lys Asp Glu Leu Ser Leu Asp Lys Ala Ser
        195                 200                 205

Ala Leu Lys Asp Ser Lys Ile Glu Ala Val Ala Glu Lys Ser Ser
    210                 215                 220

Ile Ala Lys Ile Ala Asn Leu Gln Pro Glu Val Asp Pro Lys Ala Asp
225                 230                 235                 240

Leu Tyr Phe Tyr Pro Lys Gly Asp Asp Leu Gln Leu Val Tyr Val Thr
                245                 250                 255

Glu Val Asn Val Leu Glu Pro Ala Pro Leu Arg Thr Arg Tyr Ile Ile
            260                 265                 270

Asp Ala Asn Asp Gly Ser Ile Val Phe Gln Tyr Asp Ile Ile Asn Glu
        275                 280                 285

Ala Thr Gly Thr Gly Lys Gly Val Leu Gly Asp Thr Lys Ser Phe Thr
    290                 295                 300

Thr Thr Ala Ser Gly Ser Ser Tyr Gln Leu Lys Asp Thr Thr Arg Gly
305                 310                 315                 320

Asn Gly Val Val Thr Tyr Thr Ala Ser Asn Arg Gln Ser Ile Pro Gly
                325                 330                 335

Thr Ile Leu Thr Asp Ala Asp Asn Val Trp Asn Asp Pro Ala Gly Val
            340                 345                 350
```

```
Asp Ala His Thr Tyr Ala Ala Lys Thr Tyr Asp Tyr Tyr Lys Ala Lys
            355                 360                 365

Phe Gly Arg Asn Ser Ile Asp Gly Arg Gly Leu Gln Leu Arg Ser Thr
    370                 375                 380

Val His Tyr Gly Ser Arg Tyr Asn Asn Ala Phe Trp Asn Gly Ser Gln
385                 390                 395                 400

Met Thr Tyr Gly Asp Gly Asp Gly Ser Thr Phe Ile Ala Phe Ser Gly
                405                 410                 415

Asp Pro Asp Val Val Gly His Glu Leu Thr His Gly Val Thr Glu Tyr
                420                 425                 430

Thr Ser Asn Leu Glu Tyr Tyr Gly Glu Ser Gly Ala Leu Asn Glu Ala
            435                 440                 445

Phe Ser Asp Val Ile Gly Asn Asp Ile Gln Arg Lys Asn Trp Leu Val
    450                 455                 460

Gly Asp Asp Ile Tyr Thr Pro Asn Ile Ala Gly Asp Ala Leu Arg Ser
465                 470                 475                 480

Met Ser Asn Pro Thr Leu Tyr Asp Gln Pro Asp His Tyr Ser Asn Leu
                485                 490                 495

Tyr Thr Gly Ser Ser Asp Asn Gly Gly Val His Thr Asn Ser Gly Ile
            500                 505                 510

Ile Asn Lys Ala Tyr Tyr Leu Leu Ala Gln Gly Gly Thr Phe His Gly
    515                 520                 525

Val Thr Val Asn Gly Ile Gly Arg Asp Ala Ala Val Gln Ile Tyr Tyr
    530                 535                 540

Ser Ala Phe Thr Asn Tyr Leu Thr Ser Ser Ser Asp Phe Ser Asn Ala
545                 550                 555                 560

Arg Ala Ala Val Ile Gln Ala Ala Lys Asp Gln Tyr Gly Ala Asn Ser
                565                 570                 575

Ala Glu Ala Thr Ala Ala Ala Lys Ser Phe Asp Ala Val Gly Val Asn
                580                 585                 590

<210> SEQ ID NO 8
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Predicted N-terminal amino acid sequence of
      Bacillus polymyxa 72 neutral protease

<400> SEQUENCE: 8

Asn Glu Ala Thr Gly Lys Gly Val Leu Gly Asp Ser Lys Ser Phe
1               5                   10                  15
```